(12) United States Patent
Priem et al.

(10) Patent No.: US 10,196,421 B2
(45) Date of Patent: Feb. 5, 2019

(54) NUCLEOPHILE-REACTIVE SULFONATED COMPOUNDS FOR THE (RADIO)LABELLING OF (BIO)MOLECULES; PRECURSORS AND CONJUGATES THEREOF

(71) Applicant: Advanced Accelerator Applications SA, Saint Genis Pouilly (FR)

(72) Inventors: Thomas Priem, Caen (FR); Cedric Bouteiller, Vulbens (FR); Davide Camporese, Saint Genis Pouilly (FR); Anthony Romieu, Rouen (FR); Pierre-Yves Renard, Paris (FR)

(73) Assignee: Advanced Accelerator Applications SA, Saint Genis Pouilly (FR)

( * ) Notice: Subject to any disclaimer, the term of this patent is extended or adjusted under 35 U.S.C. 154(b) by 0 days.

(21) Appl. No.: 15/434,095

(22) Filed: Feb. 16, 2017

(65) Prior Publication Data
US 2017/0158731 A1  Jun. 8, 2017

Related U.S. Application Data

(62) Division of application No. 14/647,144, filed as application No. PCT/EP2013/074501 on Nov. 22, 2013, now Pat. No. 9,611,215.

(30) Foreign Application Priority Data

Nov. 26, 2012  (EP) .................................... 12194287

(51) Int. Cl.

| | |
|---|---|
| C07K 1/13 | (2006.01) |
| C07D 327/04 | (2006.01) |
| C07C 309/24 | (2006.01) |
| C07B 59/00 | (2006.01) |
| C07D 207/404 | (2006.01) |
| C07D 209/60 | (2006.01) |
| C07D 249/18 | (2006.01) |
| C07D 207/46 | (2006.01) |
| C07C 309/22 | (2006.01) |
| C07K 7/08 | (2006.01) |
| C07C 303/22 | (2006.01) |

(52) U.S. Cl.
CPC .............. C07K 1/13 (2013.01); C07B 59/00 (2013.01); C07B 59/001 (2013.01); C07B 59/002 (2013.01); C07C 303/22 (2013.01); C07C 309/22 (2013.01); C07C 309/24 (2013.01); C07D 207/404 (2013.01); C07D 207/46 (2013.01); C07D 209/60 (2013.01); C07D 327/04 (2013.01); C07K 7/08 (2013.01); C07B 2200/05 (2013.01)

(58) Field of Classification Search
CPC ... C07B 59/001; C07B 59/002; C07C 303/22; C07C 309/22; C07C 309/24; C07D 207/404; C07D 207/46; C07D 249/18
See application file for complete search history.

(56) References Cited

FOREIGN PATENT DOCUMENTS

| EP | 2322514 | 5/2011 |
|---|---|---|
| WO | 2011018467 | 2/2011 |

OTHER PUBLICATIONS

Crawley et al. (Organic Letters (2005) vol. 7, No. 22; 5067-5069).*
Meiners et al., "A General Route to the Monomeric Subunits of the Macrotetrolides—A Short Synthesis of Methyl Nonacetate," Eur. J. Org. Chem. 2073 (1998).
Rehse et al., "Warfarin-analogous 1,2-Oxathiolane Derivatives," 313 Arch. Pharm. (Weinheim) 773 (1980).
Priem et al., "Synthesis and Reactivity of a bis-Sulfone Cross-linker for Peptide Conjugation and [18F]-Radiolabelling Via Unusual "Double Click" Approach," 10 Org. Biomol.Chem. 1068 (Feb. 2012).
Schmitt et al., "Sulfone Opening With [18F]fluoride: An Efficient 18F-Labelling Strategy for PET Imaging," 47 Chem. Commun. 11465 (2011).
Bakiva et al., "Properties of Solutions of Disodium, Sodium-magnesium and Magnesium Salts of the Monoesters of Sulfosuccinic Acid," 35 Maslozhirovaya Promyshlennost 17 (1969) (Abstract only).

* cited by examiner

*Primary Examiner* — Valerie Rodriguez-Garcia
(74) *Attorney, Agent, or Firm* — James C. Lydon

(57) ABSTRACT

Nucleophile-reactive sulfonated compounds used as precursors to (radio)labelled (bio)molecules are produced by pre-introduction of a nucleophilic compound R* through an unusual nucleophile-induced ring-opening reaction of the sultone moiety of the precursor. The precursors and compounds conform to respective formulae (Ip) and (I):

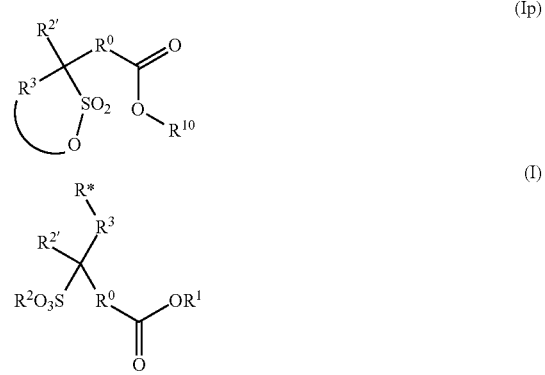

Also disclosed are methods for producing these precursors and compounds, as well as for conjugation of these compounds with (bio)molecules, and to the drugs obtained by this method.

4 Claims, No Drawings

NUCLEOPHILE-REACTIVE SULFONATED COMPOUNDS FOR THE (RADIO)LABELLING OF (BIO)MOLECULES; PRECURSORS AND CONJUGATES THEREOF

FIELD OF THE INVENTION

The field of the invention is that of (radio)labelling of complex and fragile (bio)active (macro)molecules, such as peptides, proteins, (bio)polymers, antibodies, oligonucleotides, nucleic acids, carbohydrates, lipids, used as (radio) pharmaceuticals.

The invention particularly relates to new labelling compounds capable of conjugation with these bioactive (macro) molecules. These labelling compounds form functionalised prosthetic group carrying a chosen radionuclide, in the case of radiolabelling.

The invention also concerns some new precursors of these radiolabelling compounds, the synthesis methods of these precursors, compounds and conjugates (labelling strategies) as well as the use thereof, preferably of the radiolabelled ones, in therapy (nuclear medicine i.a.) and/or in diagnosis (nuclear imaging i.a.) depending on the radioelement.

Diagnostic probes for medical imaging, especially by PET (Positron Emission Tomography), SPECT (Single Photon Emission Computed Tomography) or NIRF (Near-infrared fluorescence), are notably contemplated in this invention.

BACKGROUND ART

The radiolabelling of (bio)molecules with Fluorine-18 ($^{18}$F), is widely spread. A common PET diagnostic probe is [$^{18}$F]-labeled fluorodeoxyglucose ([$^{18}$F]-FDG):

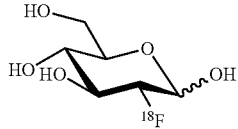

[$^{18}$F]-FDG is widely used for early detection of cancer.
[$^{18}$F]-FDG is routinely obtained by direct labelling of a mannose derivative via nucleophilic substitution.

Similarly to the carbohydrates, the peptides, proteins and the largest part of biomolecules contain numerous labile protons due to the presence of different functional groups such as hydroxyls, amides, amines, thiols, acids. However, for these kinds of macromolecules, a chemical protection of all of the functional groups cannot always be envisaged. Therefore, most often the direct labelling of these (bio) molecules by direct nucleophilic substitution cannot be performed.

The introduction of a radionuclide such as Fluorine-18 into a (bio)macromolecule of different nature, e. g. peptides, proteins, oligonucleotides, oligosaccharides is most often carried out via a prosthetic group bearing the radioisotope. This approach then involves the preparation of a functionalized and radiolabelled prosthetic compound followed by its conjugation with a specific reactive function of the (bio)macromolecule. This strategy has the advantage of making it possible to use severe conditions for the preparation of the radiolabelled prosthetic compound followed by its conjugation to the macromolecule under mild conditions preserving the integrity of the macromolecule.

A certain number of prosthetic compounds (also called prosthetic groups) labelled with Fluorine-18 are described in the literature. They can be classified according to their own reactive function and/or according to the reactive function present on the macromolecule they will react with (amines, hydrazines, oximes, acids, aldehydes etc.). Some of the prosthetic groups are designed to be coupled directly to a peptide or a protein via formation of an amide linkage using an amine function of an amino acid residue (e.g. N-terminal α-NH$_2$ or internal ε-NH$_2$ of a lysine) or optionally via any other spacer containing an amino function. In these cases, the prosthetic groups are characterized by a carboxylic function (e.g. [$^{18}$F]-FBA) usually activated as an active derivative (e.g. succinimidyl or nitrophenyl ester of the corresponding carboxylic acid).

All these radiolabelled prosthetic compounds are characterized by different synthesis criteria such as the nature and ease of synthesis of the radiolabelling precursor, the effectiveness of the fluorination stage, the total number of radiosynthesis stages, the time of synthesis, their overall radiochemical yield, the ease of purification, their effectiveness in the conjugation reaction and the in vivo stability of the corresponding bioconjugates.

Moreover, the large scale production of these radiolabelled compounds is faced with constraints related to the complete automation of their synthesis. In fact, a complete automated synthesis of those radiolabelled compounds will satisfy both the pharmaceutical standards procedures (GMP), as well as the radiological protection requirements. Therefore an ideal manufacturing procedure will be characterized by few and easy synthesis and purifications steps.

Here below are shortly reported the synthesis of two of the prosthetic groups described in the literature:
the [$^{18}$F]-SFB (N-succinimidyl 4-[$^{18}$F]-fluorobenzoate ester):

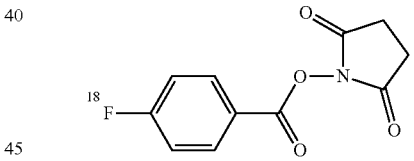

Recently, EP2404903A1 described a three-step automated method for synthesizing [$^{18}$F]-SFB using microsynthesis technique:

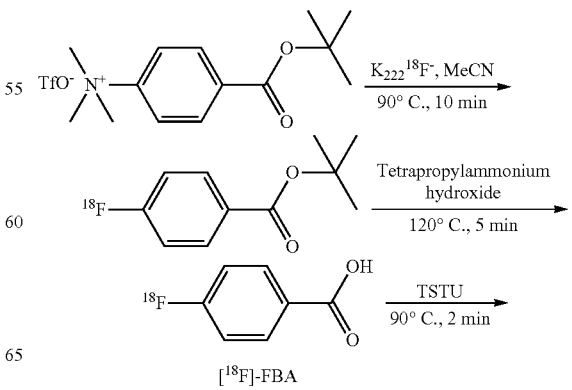

-continued

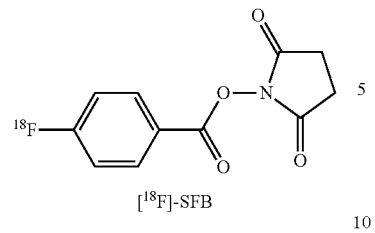

[¹⁸F]-SFB

Where:
"K222" corresponds to (4,7,13,16,21,24-Hexaoxa-1,10-diazabicyclo[8.8.8]-hexacosane
"TSTU" corresponds to: (O—(N-succinimidyl)-N,N,N',N'-tetramethyluronium tetrafluoroborate.

Even if this automated radiosynthesis leads to reasonable radiochemical decay corrected yields (60%), it has several disadvantages. It is not so easy to separate the labelled intermediate (fluoro benzoic ester) from the by product originated from the ammonium precursors. Moreover, the large number of steps and the necessity to purify each intermediate make the automation of this process difficult even if it is necessary to reach the Good Manufacturing Practice conditions.

A further not insignificant drawback is the lipophilic character of [¹⁸F]-SFB reagent which makes difficult its "wet" conjugation to water-soluble amine-containing biomolecules and the purification step (HPLC or solid-phase extraction) of the resulting [¹⁸F]-labelled molecular bioprobes.

The [¹⁸F]-SFS (1-{4-[(2,2-dioxido-1,2-oxathiolan-3-yl) carbonyl]phenyl}-4-fluoro-1-oxobutane-2-sulfonic acid):

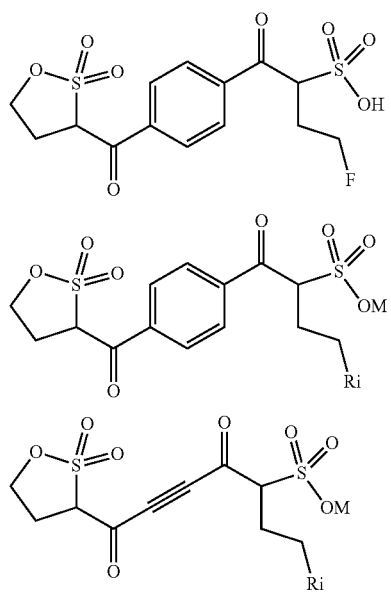

WO2011/018467A1 relates to polysultone derivatives used as precursors to radiolabelled macromolecules for medical applications especially in nuclear imaging and therapy.

Non radiolabelled Precursors

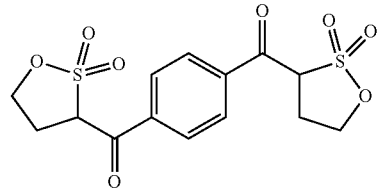

1a

1b (Radio)labelled intermediates (prosthetic groups)

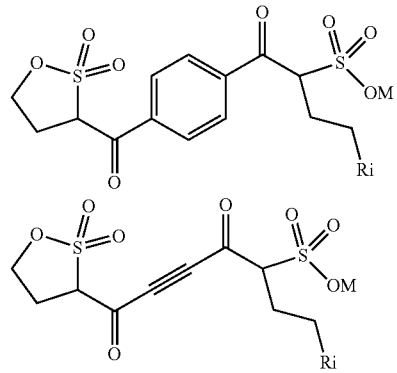

Where Ri is e.g. a radioelement or an NIR (Near Infra Red) agent
Where M is e.g. a generic cation Labelled (bio)conjugates

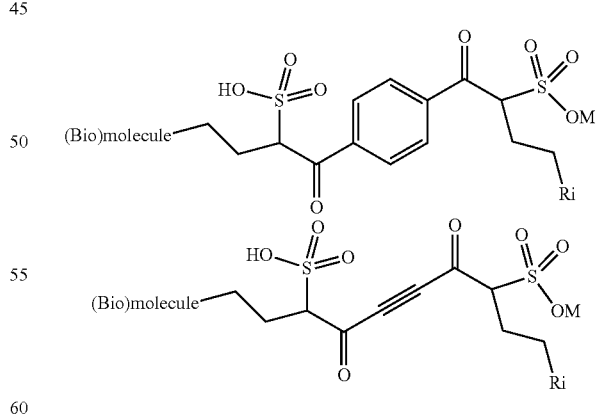

The main advantage of these polysultones is that they can be coupled with a large sort of (bio)molecules. In fact, they can be used not only for the coupling with amino functions but also with thiol and hydroxyl functions. The fast hydrolysis of these polysultone derivatives represents the main disadvantage of those prosthetic groups.

Objectives and Technical Problem

The present invention aims to combine the advantages of the above mentioned prosthetic groups avoiding their disadvantages by satisfying at least one of the following objectives:

i) To provide novel compounds, the synthesis of which is straightforward, easy, time-unconsuming, cheap and automatable, and which are capable of constituting non-labelled reactive precursors of synthons (prosthetic groups) for (radio)labelling complex and fragile—especially water-soluble and more especially amine-containing-(bio)molecules, in order to produce economical and effective (radio)pharmaceuticals.

ii) To provide novel prosthetic groups, the synthesis of which is straightforward, easy, time-unconsuming, cheap and automatable, and which are capable of constituting (radio)labelled intermediates for labelling complex and fragile—especially water-soluble and more especially amine-containing—(bio)molecules in order to produce economical and effective (radio)pharmaceuticals.

iii) To provide novel labelled conjugates of complex and fragile—especially water-soluble and more especially amine-containing—(bio)molecules useful as effective (radio)pharmaceuticals, and obtained from prosthetic compounds, the synthesis of which is straightforward, easy, time-unconsuming, cheap and automatable.

iv) To provide a novel, easy, time-unconsuming, cheap and automatable method for synthesis of the precursor of the prosthetic group (non-labelled reactive precursors) as referred to in (i) supra.

v) To provide a novel, easy, time-unconsuming, cheap and automatable method for synthesis of the novel labelled prosthetic intermediate (labelled reactive precursors) as referred to in (ii) supra.

vi) To provide a novel method for obtaining novel (radio) labelled conjugates as referred to in (iii) supra, by labelling complex and fragile—especially water-soluble and more especially amine-containing—(bio)molecules, via coupling with a (radio)labelled prosthetic compound (labelled reactive intermediate) as referred to in (ii) supra, in order to produce economical and effective (radio)pharmaceuticals; said method offering at least one of the following advantages:
- a reduction in synthesis stages,
- an increase in (radio)chemical yields at room temperatures (RT) and within very short reaction time,
- ease of separation of the intermediate and final product,
- no production of by-products,
- suitability for (radio)labelling different (bio)molecules,
- possibility of carrying out the coupling of the (radio) labelled intermediate with the (bio)molecule in water.

vii) To provide novel drugs and/or effective and economical (radio)tracers, from these new compounds as referred to in (i) & (ii) supra and conjugates as referred to in (iii) supra and this new (bio)molecule (radio)labelling method as referred to in (vi) supra.

viii) To provide a novel use of these new compounds as referred to in (i) & (ii) supra for (radio)labelling (bio) molecules with a nucleophilicradionuclide or NIR imaging agent.

ix) To provide a novel use of these new compounds as referred to in (i) & (ii) supra, for imparting water-solubility to (bio)molecules bearing at least one nucleophilic group.

BRIEF DESCRIPTION OF THE INVENTION

These objectives, among others, are satisfied by the following invention.

In a first aspect, this invention relates to new compounds of formula:

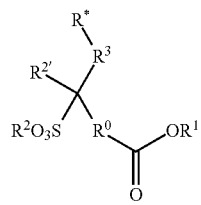

(I)

in which:

the $R^0$ bi-functional group is a spacer, preferably but not exclusively chosen among the following radicals:

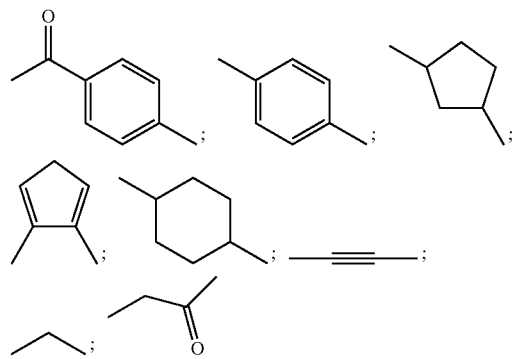

the $R^1$ monovalent hydrocarbon group is an activating group of the oxygen atom of the ester function, $R^1$ preferably corresponding to a succinimidyl ester, a benzotriazole ester, a paranitrophenyl ester or a protecting labile (preferably acid-labile) function or hydrogen;

the $R^2$ monovalent group corresponds to a hydrogen, a metallic cation, an alkyl, a cyclo-alkyl, an aryl, an arylalkyl, an alkylaryl, an acyl, an alkenyl, an alkynyl radical or a combination of these radicals; hydrogen being preferred;

the $R^{2'}$ monovalent group, corresponds to an hydrogen or an alkyl, a cyclo-alkyl, an aryl, an arylalkyl, an alkylaryl, an acyl, an alkenyl, an alkynyl radical or a combination of these radicals; hydrogen being preferred;

the $R^3$ bi-functional group corresponds to a hydrocarbon moiety, preferably to a radical —$(CR^4R^5)_n$—, wherein $R^4$, $R^5$ represents individually hydrogen or an alkyl, a cyclo-alkyl, an aryl, an arylalkyl, an alkylaryl, an acyl, an alkenyl, an alkynyl radical or a combination of these radicals; preferably hydrogen; n is preferably but not exclusively an integer between 1 and 3;

$R^*$ is a nucleophilic radical preferably containing at least one (radio)nuclide, preferably but not exclusively selected from the list fluorine-18, bromine-76, iodine-123, iodine-124, iodine-131 or characterized by NIR properties.

The compounds according to the invention are:
Preferably compounds of general formula:

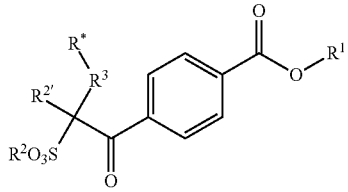
(II)

wherein
$R^1$, $R^2$; $R^{2'}$; $R^4$; $R^5$ and $R^*$ are as defined above.
and more preferably compounds of general formula:

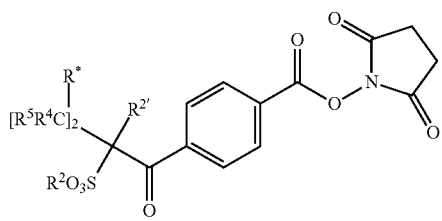
(III)

wherein
$R^2$; $R^{2'}$; $R^4$; $R^5$ and $R^*$ are as defined above, $R^2$; $R^{2'}$; $R^4$; $R^5$ preferably corresponding to hydrogen.

An example of these new compounds which is simply, economically and rapidly obtainable through an optimised multi-step protocol, is a mono-fluorinated prosthetic compound of formula (III) wherein $R^*$ is fluorine, said compound being able as its analogues, to radiolabel complex and fragile amine-containing (bio)molecules.

The sulfonate function of these compounds (I); (II); (III) not only make them soluble in water but also allows an easy separation from their apolar precursors.

In a second aspect, the invention also pertains to the precursors of formula:

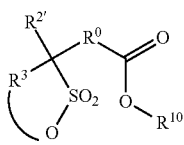
(Ip)

wherein
$R^0$; $R^3$ are as defined above;
$R^{10}$ is a protective monovalent group that avoid any side reaction on the carboxylic function and that makes possible the reaction of the precursor (Ip) with a $R^*$ bearing nucleophilic compound and corresponds to an alkyl, a cyclo-alkyl or possibly a hydrogen or to $R^1$ as above defined, in case where $R^1$ permits the reaction of the precursor (Ip) with a $R^*$ bearing nucleophilic compound;
the functional units of formula $COOR^{10}$ and

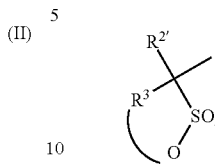

being nucleophile-reactive, the nucleophilic reactivity of these functional units being different, $COOR^{10}$'s nucleophilic reactivity being preferably less than the nucleophilic reactivity of

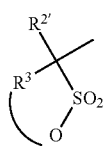

Preferably, these precursors are those of formula:

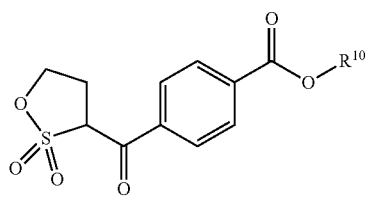
(Ip)

wherein
$R^{10}$ is a monovalent group as defined above;
the functional units of formula $COOR^{10}$ and

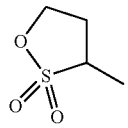

being nucleophile-reactive, the nucleophilic reactivity of these functional units being different, $R^{10}$'s nucleophilic reactivity being preferably less than the nucleophilic reactivity of

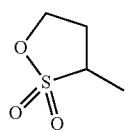

The sultone and the $COOR^{10}$ nucleophile-reactive functional moieties within the same (e.g. benzenic) scaffold makes it possible to reach the required chemical orthogonality between these moieties through a simple/easy/time-unconsuming protecting group strategy fully compatible with the requirements of automation.

In a third aspect, a subject of the invention is a method for synthesis of the precursors (Ip) or (IIp) as above defined, characterized in that it essentially consists in:

i) implementing a structure, containing an ester and at least a second reactive function, of formula:

(IV)

wherein
the $R^0$ bi-functional group is as defined supra;
X is the second reactive function suitable to act as a leaving group during a nucleophilic substitution. X is preferably but not exclusively an alkoxide function, an halogen as chlorine, bromine, iodine or a triflate, a tosylate or a mesylate.
the $R^{10'}$ monovalent group corresponds preferably but not exclusively to an alkyl or a cyclo-alkyl, one of the ester functions $OR^{10''}$ or an hydrogen ii) making the structure (IV) react with:
at least one sultone—advantageously a butane sultone, propane sultone and/or an ethane sultone—, the sultone being preferably firstly metalated by means of a deprotonating agent, preferably n-butyl-lithium, then acylated;
and with a protecting reagent capable of substituting the $R^{10'}$ function in (IV) by a protecting labile, preferably acid-labile, function $R^{10''}$.

In a fourth aspect, a subject of the invention is a method for the synthesis of the compounds (I); (II) & (III) derived from the sultone precursors (Ip), characterized in that it comprises the following stages:

a. utilization or synthesis of a precursor (Ip), or obtained by the method as above defined;
b. opening of the sultone of the precursor with a R* bearing nucleophilic radical leading to the formation of a sulphonate, being preferably carried out either in a polar protic typically as alcohols solvent or in the presence of a polar aprotic solvent which more preferably contains some water in an amount—given in an increasing order of preference and in % w/w—of less than or equal to 15; 10; 8; 6; 5; comprised between 1-4; 2-4;
c. deprotection of the protected labile ester function;
d. activation of the carboxylic function obtained as mentioned on point c. by grafting of a $R^1$ monovalent group as defined supra;
e. recovery of the sulphonated nucleophilic-reactive compound obtained in stage d.

In a fifth aspect, the invention relates to the conjugates made from the compounds (I); (II) & (III) and at least one active (bio)molecule as well as to the process for making these conjugates.

In a sixth aspect, the invention relates to a drug comprising at least one compound according to the invention or obtained by one of the methods according to the invention.

In a seventh aspect, the invention relates to the use of the compounds according to the invention or obtained by the method according to the invention for (radio)labelling (bio) molecules with nucleophilic radionuclides or Near Infra Red (NIR) agents, or for imparting water-solubility to (bio)molecules bearing at least one nucleophilic group.

The main advantages of the invention are the following:
Use of the same approach for (radio)labelling irrespective of the radionuclide, NIR agent or labelling agent;
Obtaining high (radio)chemical yields in mild conditions (at room temperatures and within very short reaction time);
Possibility of easily separate the starting precursor (apolar) from the product formed (polar);
No production of by-products;
Possibility of automation of the complete synthesis procedure;
Suitability for labelling numerous and various (bio)macromolecules;
Possibility to conjugate with the (bio)molecules in aqueous conditions;
Simplicity;
Economy;
Access to novel compounds opening up multiple therapeutic and diagnostic developments.

DETAILED DESCRIPTION OF THE INVENTION

Definitions

According to the terminology of this text, the following non limitative definitions have to be taken into consideration:

Every singular designates a plural and reciprocally.
"(bio) molecules" or "biomolecules" refers notably to biological macromolecules, such as peptides, proteins, antibodies, oligonucleotides, nucleic acids, carbohydrates, lipids, nanoparticles, biopolymers, and dendrimers.
"prosthetic" means a functionalised group or a functionalised compound which is intended to or is conjugated (tightly bound) with complex and fragile (bio)molecules, which could be a nonpolypeptide structure and which could or not be required for the activity of the (bio)molecule. This conjugate could be a radiotracer wherein the prosthetic group carries the chosen radionuclide.
In the formulae, notably those of the novel compounds (I); (II); (III); (Ip); (IIp), reference is made to the following definitions:
"alkyl" corresponds for example to a linear, branched or cyclic saturated monovalent C1-C30 alkyl group, preferably C1-C20, and, even more preferentially C1-C10, optionally substituted, comprising or not comprising heteroatoms. Examples of alkyl groups are in particular methyl, ethyl, isopropyl, n-propyl, tert-butyl, isobutyl, n-butyl, n-pentyl, isoamyl and 1,1-dimethylpropyl.
"aryl" corresponds for example to one or more monocyclic or polycyclic and preferably monocyclic or bicyclic condensed or uncondensed aromatic monovalent groups, having 6 to 18 carbon atoms. It must be understood that, within the framework of the invention, by polycyclic aromatic radical is meant a radical having two or more aromatic rings, condensed (orthocondensed or ortho- and pericondensed) with each other, i.e. having, in pairs, at least two carbon atoms in common. Said aromatic hydrocarbon group ("aryl") is optionally substituted for example by one or more $C_1$-$C_3$ alkyls, one or more halogenated hydrocarbon radicals (e.g. $CF_3$), one or more alkoxy (e.g. $CH_3O$) or one or more hydrocarbon radicals comprising one or more ketone units (e.g. CH₃CO—). By way of examples of aryls, there can be mentioned the phenyl, naphthyl, anthryl and phenanthryl radicals.

"arylalkyl" corresponds for example to an alkyl group as defined above, substituted by one or more aryl groups on its hydrocarbon chain, the aryl group being as defined above. Examples of this are benzyl and triphenylmethyl.

"alkylaryl" corresponds for example to monovalent alkyl, substituted or linked to one or more monovalent aromatic groups, optionally substituted.

By "acyl" is meant an R⁰—CO— group where R₀ represents alkyl as defined above; or an Ar—CO— group where Ar represents an aryl group as defined above, or arylalkyl in which aryl and alkyl are as defined above and in which the aryl part is optionally substituted e.g. by alkyl.

By "cycloalkyl" is meant a mono- or polycyclic, preferably mono- or bicyclic, saturated hydrocarbon radical preferably having from 3 to 10 carbon atoms, even better from 3 to 8. By polycyclic saturated hydrocarbon radical is meant a radical having two or more cyclic rings attached to each other by a bonds and/or condensed in pairs. Examples of polycyclic cycloalkyl groups are adamantane and norbornane. Examples of monocyclic cycloalkyl groups are cyclopropyl, cyclobutyl, cyclopentyl, cyclohexyl, cycloheptyl and cyclooctyl.

By "alkenyl" is meant e.g. a substituted or unsubstituted, linear or branched, unsaturated hydrocarbon chain, having at least one olefinic double bond, and more preferably a single double bond. Preferably, the alkenyl group has 2 to 8 carbon atoms, even better 2 to 6. This hydrocarbon chain optionally comprises at least one heteroatom such as O, N, S. Preferred examples of alkenyl groups are the allyl and homoallyl groups.

By "alkynyl" is meant e.g. according to the invention, a substituted or unsubstituted, linear or branched, unsaturated hydrocarbon chain, having at least one acetylenic triple bond, and more preferably a single triple bond. Preferably, the alkynyl group has 2 to 8 carbon atoms, even better 2 to 6 carbon atoms. By way of example, there can be mentioned the acetylenyl group, as well as the propargyl group. This hydrocarbon chain optionally comprises at least one heteroatom such as O, N, S.

Preferences

The Compounds and their Precursors According to the Invention:

Spacer R⁰ corresponds to

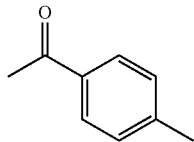

Compounds (I); (II); (III) are for example:

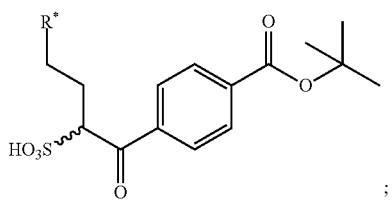

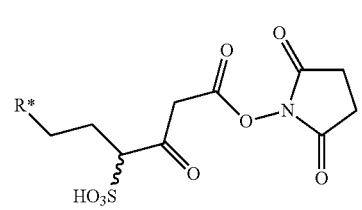

R* is preferably ¹⁸F

Precursor (Ip) corresponds to:

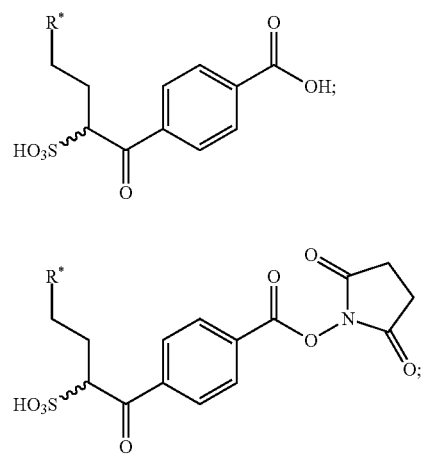

Spacer R⁰ corresponds to —CH₂C(O)—

Compounds (I); (II); (III) are for example:

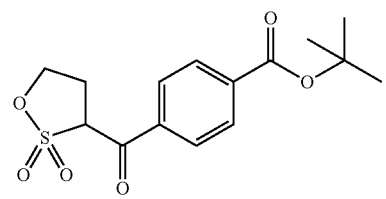 [SMILES: CC(C)(C)OC(=O)c1ccc(C(=O)C2CCOS2(=O)=O)cc1]

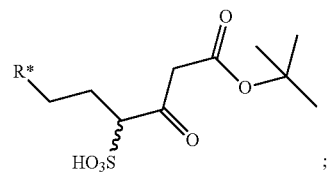

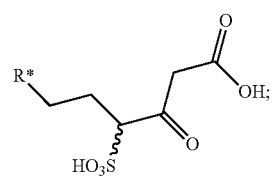

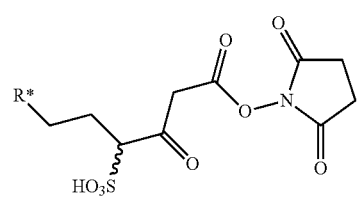

R* is preferably ¹⁸F

Precursors (Ip) is:

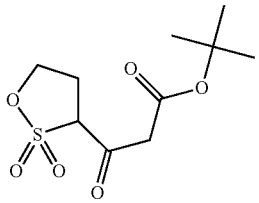 [SMILES: CC(C)(C)OC(=O)CC(=O)C1CCOS1(=O)=O]

Spacer R⁰ corresponds to

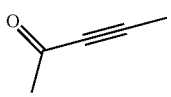

Compounds (I); (II); (III) are for example:

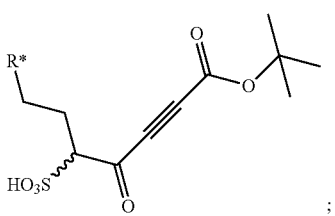
;

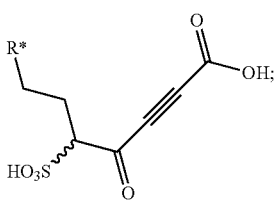

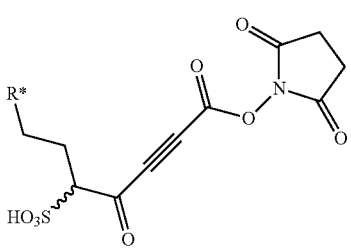

Precursors (Ip) corresponds e.g. to:

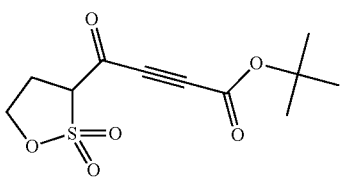 [SMILES: CC(C)(C)OC(=O)C#CC(=O)C1CCOS1(=O)=O]

Spacer R⁰ corresponds to

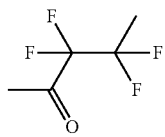

Compounds (I); (II); (III) are for example:

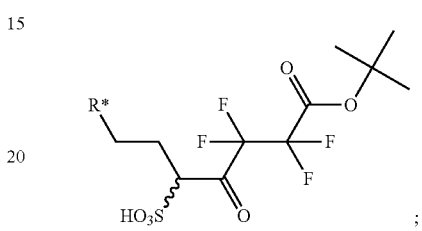
;

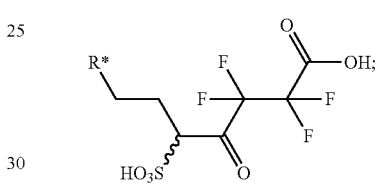

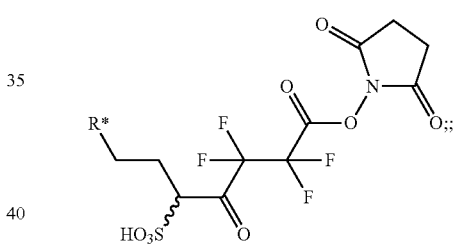
;;

Precursors (Ip) e.g. is:

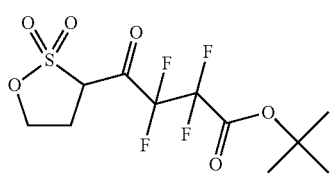 [SMILES: CC(C)(C)OC(=O)C(F)(F)C(F)(F)C(=O)C1CCOS1(=O)=O]

Synthesis of Precursors (Ip)

These precursors can be synthesized from commercial products.

Thus, the method for synthesizing the precursors (Ip) essentially consists in making react, preferably, a monoester of a dicarboxylic product, in particular an aromatic dicarboxylic product (e.g. terephthalic acid), the $CO_2H$ moiety of which being protected through an acid-labile group namely tert-butyl ester, with a sultone metalated with n-BuLi and subsequently acylated. For example, this synthesis can be summarized on the scheme 1 as follows:

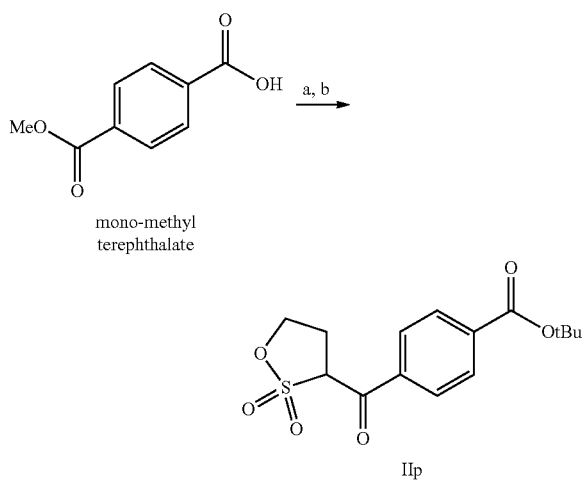

mono-methyl terephthalate

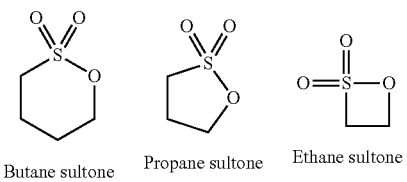 [SMILES: O=S1(=O)CCCCO1 ; O=S1(=O)CCCO1 ; O=S1(=O)CCO1]

IIp

Scheme 1 Reagents and conditions: (a) tert-butyl 2,2,2-trichloroacetamidate, $CH_2Cl_2$, 35° C., overnight; (b) 1,3-propanesultone, n-BuLi, THF, −78° C., 3 h 30 then acetic acid, THF, −78° C. to rt, overall yield 51%.

Butane sultones and/or ethane sultones can be used instead of or in addition to propane sultones:

Butane sultone    Propane sultone    Ethane sultone

Synthesis of the Compounds (I); (II); (III)

According to the invention, the method for obtaining the novel compounds (I); (II); (III) is preferably done from the precursors (Ip), (IIp) according to a three-stage synthetic scheme:

1. Introduction of the R* radical, for example fluorination of (IIp) by means of a R* (e.g. fluorine) bearing reagent (e.g KF/Kryptofix [K222]), to obtain efficiently the desired R* (e.g. fluoro)-sulfonated derivative (II);

The reaction solvent can be a polar aprotic solvent containing traces of water (e.g. 3%) or a protic solvent;
  the polar aprotic solvent being preferably but not exclusively selected among the followings: acetonitrile, dimethylsulfoxide (DMSO), dimethylformamide (DMF), tetrahydrofuran (THF), toluene or a mixture of them;
  the protic solvent being preferably but not exclusively selected among the alcohols, and advantageously among the group of alcohols comprising—preferably but not exclusively composed of MeOH, EtOH, i-PrOH, t-BuOH, Amyl alcohol, or a mixture of them;
[stage 1 corresponds to the steps a & b of the method for obtaining the novel compounds (I); (II); (III) according to the claims].

2. Removal of the $R^1$ corresponding to $R^{10'''}$ radical (e.g tert-butyl) of the R* (e.g.fluoro)-sulfonated derivative (II) by treatment, such as hydrolysis (e.g with a 25% TriFluroAcetic acid solution in $CH_2Cl_2$) or hydrogenolysis, depending on the protecting agent, to give a free (e.g benzoic) acid (II) wherein $R^1$ corresponding to hydrogen.

[stage 2 corresponds to the step c of the method for obtaining the novel compounds (I); (II); (III) according to the claims].

3. Finally:
  i) Activation of the carboxylic function with an activating agent [e.g. N-HydroxySuccinimide (NHS); para-nitrophenyl] in a dry polar aprotic solvent (e.g $CH_3CN$);
  ii) or reaction of R* (e.g.fluoro)-sulfonated free (e.g benzoic) acid (II) wherein $R^1$ corresponding to hydrogen, with a coupling reagent [e.g O—(N-succinimidyl)-1,1,3,3-tetramethyluronium tetrafluoroborate (TSTU)] and a base [e.g. N,N-Diisopropylethylamine (DIEA) in a dry polar aprotic solvent [e.g. N-Methyl-2-pyrrolidone (NMP)]; led to the bioconjugatable activated ester (III) in almost quantitative yield.

[stage 3 corresponds to the step d of the method for obtaining the novel compounds (I); (II); (III) according to the claims].

The so obtained sulphonated nucleophilic-reactive compounds (II) or (III) are collected. [step e of the method for obtaining the novel compounds (I); (II); (III) according to the claims].

These details of implementation make it possible to increase the electrophilicity of the carbonyl function and to couple with nucleophilic functions such as amino acids, peptides, in mild conditions.

According to a remarkable and particular embodiment of the method for obtaining the novel compounds (I); (II); (III) according to the invention, the R* (e.g. fluorine) bearing reagent is adsorbed onto an elutable support and is afterwards eluted into a reactor wherein it reacts with the precursor (Ip).

The R* (e.g. fluorine) is eluted into the reactor by means of an eluent solution comprising at least one polar aprotic or protic solvent and at least one phase transfer agent.

The possible polar aprotic solvent of the eluent solution is preferably selected in the group comprising—even better composed of—$CH_3CN$, DMF, DMSO, THF, toluene, mixture $CH_3CN$/DMF or DMSO/water.

The possible protic solvent of the eluent solution is preferably selected in the group comprising—ideally composed of—water MeOH, EtOH, i-PrOH, t-BuOH, Amyl alcohol or a mixture of them.

The phase transfer agent is e.g. chosen between a quaternary amine (e.g. $N(C_4H_9)^+$ B) or a compound of general formula Kriptand/MxBy, wherein Kriptand is a molecule suitable for a stable coordination of the metal M and were M is an alkaline metal, alkaline earth metal and in both cases B is a counter ion as (but not only) carbonate, bicarbonate, oxalate. More preferably but not exclusively, said phase transfer agent being selected in the group comprising—ideally composed of—: K222/Na2CO3; K222/K2CO3; K222/Cs2CO3; K222/Rb2CO3; TBAHCO3; K222/K2C2O4; K222/NaHCO3; K222/KHCO3; K222/RbHCO3; K222/CsHCO3 where K222 corresponds to the kriptand (4,7,13,16,21,24-Hexaoxa-1,10-diazabicyclo[8.8.8]hexacosane) and mixtures thereof.

After removal of the eluent solvents, the precursor (IIp) is added into the reactor as solution of a protic or aprotic solvent.

The possible polar aprotic solvent used to make the (IIp) solution is preferably selected in the group comprising—even better composed of—$CH_3CN$, DMF, DMSO, THF, toluene, mixture $CH_3CN$/DMF or DMSO/water.

The possible protic solvent used to make the (IIp) solution is preferably selected in the group comprising—ideally composed of—water MeOH, EtOH, i-PrOH, t-BuOH, Amyl alcohol or a mixture of them.

Into the reactor R* (e.g. fluorine) reacts with the precursor (IIp).

In a preferred case, the reaction between the R* (e.g. fluorine) bearing reagent and the precursor (IIp) is done in preferentially less than 15 minutes, at a temperature greater or equal to the room temperature, comprised between in an increasing order of preference: 30 and 150° C.; 40 and 120° C.; 50 and 110° C.; 60 and 100° C.; 80 and 100° C.

This fluorinated intermediate is then hydrolized in order to remove the protecting group of the carboxyl function by means either of acidic or basic hydrolysis or hydrogenation. The resulting carboxylic acid derivative is then activated as reactive ester derivative by means of any coupling agent such as TSTU or the combination DCC/NHS. At this step, the active ester can either be used for direct coupling with various (bio)molecules or further purified if necessary.

Here below is reported a general scheme for the labelling of the precursor (IIp) with fluorine. The differences between the labelling with F-19 and the radiolabelling with F-18 are reported into the caption.

By way of example, this latter can be a far-red fluorescent marker: amine derived from the pentamethine cyanine 5.5 (Cy 5.5) core or a polypeptide containing lots of hydrophobic lateral chains.

The conjugation results from an amidification reaction between the NHS ester of [$^{18}$F]-(III) and a primary amino group present on the cyanine scaffold.

This conjugated amino-fluorophore is obtained through a two-steps reaction sequence (i.e., amidification followed by removal of the phthalimide protecting group) from a cyanine phthalimide-acid derivative.

The amidification comprises an amidolysis of active esters involving a base e.g. a tertiary amine such as DIEA in a dry polar aprotic solvent such as N-Methyl-2-Pyrrolidone (NMP).

The final fluorinated/sulfonated Cy 5.5 derivative is collected in a pure form after purification achieved e.g. by RP-HPLC.

Moreover the originally water insoluble precursor Cy 5.5 becames soluble in aqueous buffers thanks to the conjuga-

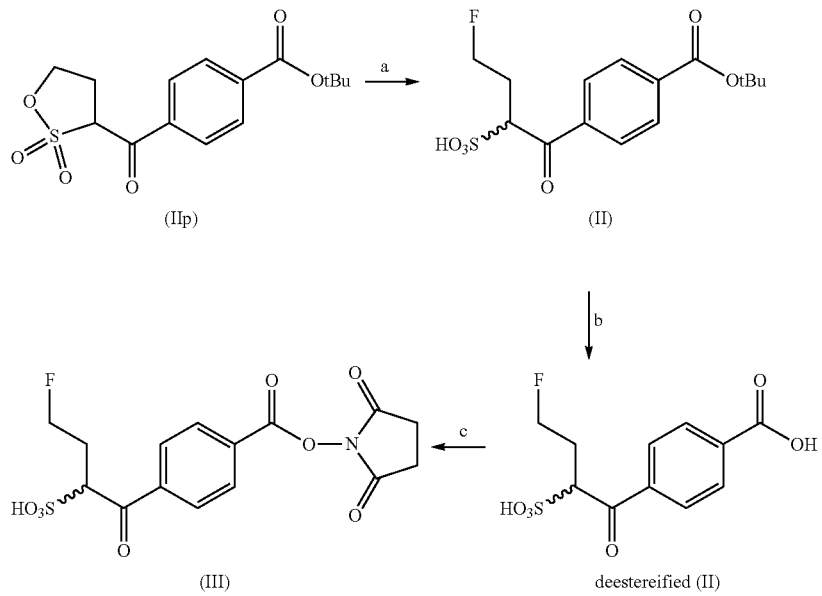

Scheme 2 Reagents and conditions:

Labelling using F-19: (a) KF, Kryptofix[K222], CH$_3$CN—H$_2$O (98:2, v/v), RT RP-HPLC purification, 63%; (b) TFA, CH$_2$Cl$_2$, RT, 1 h, quantitative yield; c) DCC, NHS, CH$_3$CN RT, 1 h or TSTU, DIEA, NMP, 30 min, quantitative yield.

Labelling using F-18(a) see Table 1, entries 6-8; (b) 4.0 M aq. HCl, 80° C., 5 min; (c) TSTU, DIEA, CH$_3$CN, 50° C., 5 min.

Conjugation of the (Radio)Labelled Compounds (I); (II); (III) with (Bio)Molecule The novel nucleophilic(amine)-reactive prosthetic compounds (I); (II); (III) are useful for (radio)labelling and imparting water-solubility of molecular architectures, e.g. of fragile and hydrophobic molecules.

Such a conjugation can be for instance implemented with an amine-reactive (bio)molecule through an amidification reaction between the compounds (I); (II); (III), especially the NHS ester of [$^{18}$F]-(III) and a primary amino group present onto the amine-reactive (bio)molecule.

tion with the very polar and hydrophilic sulfonate derivative. This fact confirms that the present invention enables to increase the hydrophilic character of the (bio)molecules conjugated therewith.

CONCLUSION

The new chemical path opened by the invention which consists in pre-introduction of a marker R*, e.g. Fluorine-18, through an unusual nucleophile-induced ring-opening reaction of the sultone (e.g. 1,3-propanesultone) moiety of an heterobifunctional precursor. This nucleophilic substitution leads to the disclosure of a free sulfonic acid moiety which is greatly beneficial, since it accelerates and facilitates the purification of the resulting R*-conjugates by drastically modifying their intrinsic hydrophilic character. Thus, these (radio)synthesis procedures can be rapidly and easily implemented and automated. They are readily reproducible and give very satisfactory yields within very short reaction times (around 1 minute). These added-values make it clear that the novel prosthetic compounds and precursors according to the invention, represent a viable alternative notably to [$^{18}$F]-SFB. Furthermore, the mild reaction conditions associated with the chemistry of the active ester (e.g. NHS active ester) enables to achieve the R* [especially $^{18}$F]-(radio)labelling of peptides or highly-functionalised and fragile fluorescent markers. Moreover, this technology when applied to an active targeting molecules permit to obtain a R*[especially F-18]-(radio)labelled compound suitable for medical applications such as nuclear imaging, optical imaging and even the combination of both of them in the case of [$^{18}$F]-PET/NIRF dual modality agents.

EXAMPLES

Unless otherwise noted, all other commercially available reagents and solvents are used without further purification. $CH_2Cl_2$ and $CH_3CN$ are dried through distillation over $P_2O_5$ and $CaH_2$ respectively. Anhydrous Tetrahydrofuran (THF) is obtained through drying over Na+/benzophenone. Anhydrous Dimethylformamide (DMF) is obtained from Carlo Erba-SdS or Fisher Scientific. Peptide synthesis-grade N-Methyl-2-pyrrolidone (NMP) is purchased from Carlo Erba-SdS. Bovine serum albumin (BSA) protein and Kryptofix[K222] (4,7,13,16,21,24-hexaoxa-1,10-diazabicyclo[8.8.8] hexacosane) are purchased from Sigma-Aldrich. TLC are carried out on Merck DC Kieselgel 60 F-254 aluminium sheets. The spots are visualised by illumination with UV lamp ($\lambda$=254 nm) and/or staining with $KMnO_4$ solution. Flash column chromatography purifications are performed on Geduran® Si 60 silica gel (40-63 µm) or (63-200 µm for cynanine derivatives) from Merck. Cyanine amino carboxamide 6 is prepared according to a synthetic scheme described in the ESI file). The synthesis of dodecapeptide (N$^\alpha$-Ac-lysine-terminated of formula: AcKGRANLRILARY is carried out on an Applied Biosystems 433A peptide synthesizer using the standard Fmoc/tBu chemistry16 and the Wang resin (Iris Biotech, loading 0.9 mmol/g) on a scale of 0.25 mmol. The HPLC-gradient grade acetonitrile ($CH_3CN$) and methanol ($CH_3OH$) are obtained from VWR. Phosphate buffered saline (PBS, 100 mM phosphate+ 150 mM NaCl, pH 7.5) and aq. mobile-phases for HPLC are prepared using water purified with a Milli-Q system (purified to 18.2 MΩ·cm). Triethylammonium bicarbonate (TEAB, 1.0 M) buffer is prepared from distilled triethylamine and CO2 gas Instruments and Methods.

NMR spectra ($^1$H, $^{13}$C and $^{19}$F) are recorded on a Bruker DPX 300 spectrometer (Bruker, Wissembourg, France) or with a Bruker AC 200. Chemical shifts are reported in parts per million (ppm) downfield from residual solvent peaks: $CDCl_3$ ($\delta_H$=7.26, $\delta_C$=77.16) or $CD_3OD$=3.31, $\delta_C$=49.0)[17] and coupling constants are reported as Hertz (Hz). Splitting patterns are designated as singlet (s), doublet (d), double doublet (dd), double double doublet (ddd) and triplet (t). Splitting patterns that could not be interpreted or easily visualised are designated as multiplet (m). $^{13}$C substitutions are determined with JMOD experiments, differentiating signals of methyl and methine carbons pointing "up" (+) from methylene and quaternary carbons pointing "down" (−).

The elemental analyses are carried out with a Flash 2000 Organic Elemental Analyzer (Thermo Scientific). Analytical HPLC is performed on a Thermo Scientific Surveyor Plus instrument equipped with a PDA detector. Semi-preparative HPLC is performed on a Thermo Scientific SPECTRASYSTEM liquid chromatography system (P4000) equipped with a UV-visible 2000 detector. Mass spectra are obtained with a Finnigan LCQ Advantage MAX (ion trap) apparatus equipped with an electrospray (ESI) source. UV-visible absorption spectra are obtained on a Varian Cary 50 scan spectrophotometer by using a rectangular quartz cell (Varian, standard cell, Open Top, 10×10 mm, 3.5 mL).

Fluorescence spectroscopic studies (emission/excitation spectra) are performed on a Varian Cary Eclipse spectrophotometer with a semi-micro quartz fluorescence cell (Hellma, 104F-QS, 10×4 mm, 1400 µL). For details related to the determination of real time quantum yields, see "Electrospray ionization", the article on Wikipedia.

Fluoride-18 is produced by the $^{18}$O[p,n]$^{18}$F nuclear reaction using a GE Medical Systems PETtrace cyclotron [18 MeV proton beam] (Advanced Accelerator Applications, Saint-Genis-Pouilly, France) and $^{18}$O-enriched water purchased from Marshall Isotopes Ltd. (98%, Tel Aviv, Israel).

Solid-phase extraction (SPE) cartridges (SepPak QMA Light, Oasis HLB and CM) are obtained from ABX advanced biochemical compounds (Radeburg, Germany) and Waters (Guyancourt, France). The HLB cartridges are always pre-conditioned with ethanol (5 mL), water (5 mL) and dried with air.

Radiosyntheses are performed on a TRACERlab MX (GE Medical Systems, Buc, France) automated synthesis unit in a shielded hot cell (8 cm lead, Comecer, Castel Bolognese, Italy).

A flow-count radio-HPLC detector system from Bioscan is used only for HPLC analyses (performed on a Dionex UltiMate® 3000 LC system) of reactions involving $^{18F}$.

HPLC Separations.

Several chromatographic systems are used for the analytical experiments and the purification steps: System A: RP-HPLC (Thermo Hypersil GOLD C18 column, 5 µm, 4.6×100 mm) with $CH_3CN$ and 0.1% aq. trifluoroacetic acid (aq. TFA, 0.1%, v/v, pH 2.0) as eluents [100% TFA (5 min), linear gradient from 0% to 80% (40 min) of CH3CN] at a flow rate of 1.0 mL min-1. Dual UV detection is achieved at 254 and 265 nm. System B: RP-HPLC (Thermo Hypersil GOLD C18 column, 5 µm, 2.1×100 mm) with CH3CN and 0.1% aq. trifluoroacetic acid (aq. TFA, 0.1%, v/v, pH 2.0) as eluents [80% TFA (5 min), linear gradient from 20% to 40% (5 min) and 40% to 100% (50 min) of $CH_3CN$] at a flow rate of 0.25 mL min-1. UV-vis detection with the "Max Plot" (i.e., chromatogram at absorbance maximum for each compound) mode (220-798 nm). System C: RP-HPLC (Thermo Hypersil GOLD C18 column, 5 µm, 10×250 mm) with $CH_3CN$ and 0.1% aq. TFA as eluents [100% TFA (5 min), linear gradient from 0% to 20% (10 min), 20% to 45% (25 min), 45% to 65% (10 min) and 65% to 100% (5 min) of CH3CN] at a flow rate of 5.0 mL min-1. Dual UV detection is achieved at 270 and 300 nm. System D: RP-HPLC (Thermo Hypersil GOLD C18 column, 5 µm, 21.2×250 mm) with CH3CN and 0.1% aq. TFA as eluents [100% TFA (5 min), linear gradient from 0% to 10% (5 min), 10% to 30% (20 mM), 30% to 50% (10 min) and 50% to 100% (15 min) of CH3CN] at a flow rate of 15.0 mL mM-1. Dual UV detection is achieved at 270 and 300 nm. System E: RP-HPLC (Varian Kromasil C18 column, 10 µm, 21.2×250) with $CH_3CN$ and aq. TEAB (50 mM, pH 7.5) as eluents [100% TEAB (5 mM), linear gradient from 0% to 30% (10 min) and 30% to 100% (70 min) of CH3CN] at a flow rate of 20 mL min-1. Dual visible detection is achieved at 625 and 680 nm. System F: system C with the following gradient [90% TFA (5 mM), linear gradient from 10% to 100% (36 min) of $CH_3CN$] at a flow rate of 4.0 mL min-1. Dual visible detection is achieved at 625 and 680 nm. System G: system A with the following gradient [80% TFA (5 min), linear gradient from 20% to 100% (40 min) of CH$_3$CN] at a flow rate of 1.0 mL min-1. Dual UV detection is achieved at 220 and 260 nm. System H: RP-HPLC (Theimo Hypersil GOLD C18 column, 5 μm, 10×100 mm) with CH3CN and 0.1% aq. TFA as eluents [100% TFA (5 min), linear gradient from 0% to 80% (40 mM) and 80% to 100% (5 min) of CH$_3$CN] at a flow rate of 4.0 mL min-1. Dual UV detection is achieved at 227 and 261 nm. System I: system A with the following gradient [100% TFA (3.8 mM), linear gradient from 0% to 44% (16.9 min) and 44% to 100% (3.8 min) of CH$_3$CN] at a flow rate of 1.3 mL mM-1. Dual UV detection is achieved at 254 and 265 nm.

Example 1: Sultone-Benzoic Acid, Tert-Butylester (2)

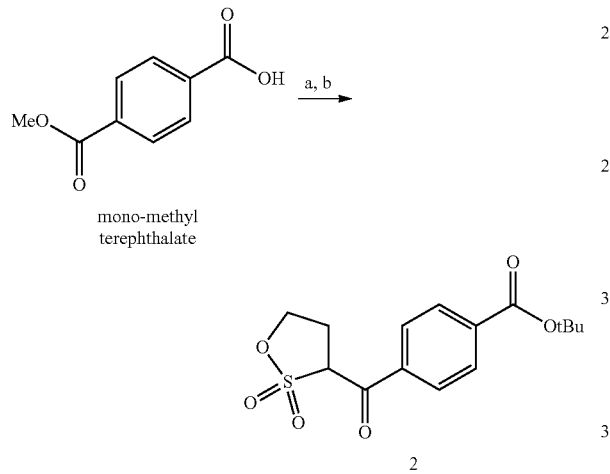

Scheme 1 Reagents and conditions: (a) tert-butyl 2,2,2-trichloroacetamidate, Cf$_2$Cl$_2$, 35° C., overnight; (b) 1,3-propanesultone, n-BuLi, THF, −78° C., 3 h 30 then acetic acid, THF, −78° C. to RT, overall yield 51%.

(a) Esterification: To a stirred solution of mono-methyl terephthalate (500 mg, 2.78 mmol, 1 equiv.) in dry CH$_2$Cl$_2$ (15 mL), under an argon atmosphere, is added tert-butyl 2,2,2-trichloroacetimidate (1.25 g, 5.55 mmol, 2 equiv.). The resulting reaction mixture is stirred at 35° C. overnight. Then, the crude mixture is filtrated to remove the remaining unreacted mono-methyl terephthalate acid and is then purified by flash-chromatography on a silica gel column using a mixture of cyclohexane-ethyl acetate (9:1, v/v) as the mobile phase. After removal of the solvent under vacuum, the resulting pure solid is directly used in the next step. TLC analysis: Rf 0.73 (cyclohexane-EtOAc, 3:7, v/v).

(b) Acylation of 1,3-propanesultone: To a stirred solution of commercial 1,3-propanesultone (720 mg, 5.89 mmol, 2.1 equiv.) in dry THF (10 mL), under an argon atmosphere, at −78° C., is added dropwise n-BuLi (2.0 M in hexane, 3 mL, 6 mmol, 2.2 equiv.). After 1 h of stirring at −78° C., a solution of the previously isolated tert-butyl methyl diester (vide supra) in dry THF (10 mL) is added dropwise to the previous vigorously stirred mixture. The resulting reaction mixture is stirred at −78° C. for 2 h 30, then kept at −78° C., and quenched by adding 1 mL of glacial acetic acid dissolved in dry THF (3 mL). Thereafter, the reaction mixture is slowly warmed up to RT then diluted with brine (20 mL) and Cf$_2$Cl$_2$ (50 mL). The product is extracted from the aq. Phase with CH$_2$Cl$_2$ (30 mL). The combined organic layers are dried over anhydrous MgSO$_4$, filtered and then concentrated under reduced pressure. The resulting crude product is then purified by flash-chromatography on a silica gel column using a mixture of cyclohexane-EtOAc (gradient from 9:1 to 7:3, v/v) as the mobile phase. The desired product 2 is isolated as a white pasty solid (458 mg, overall yield for the two steps 51%). TLC analysis: Rf 0.33 (cyclohexane-ethyl acetate, 3:7, v/v); HPLC (system A): Rt=31.4 min (purity 97%).

Example 2: Mono-Fluoro-Sulfonated Tert-Butyl Ester (3)

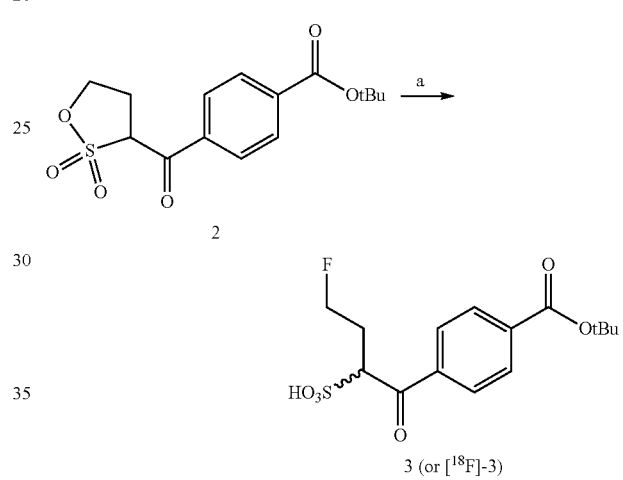

Example 2.1: Synthesis of a Non-Radioactive [$^{19}$F]Mono-Fluoro-Sulfonated Tert-Butyl Ester (3)

To a stirred solution of Kryptofix[K222] (76.2 mg, 0.20 mmol, 3.3 equiv.) and KF (10.7 mg, 0.184 mmol, 3 equiv.) in a mixture of dry CH$_3$CN (1 mL) and deionised water (20 μL), is added sultone 2 (20 mg, 0.061 mmol, 1 equiv.). The resulting reaction mixture is stirred at room temperature and its completion is checked by analytical RP-HPLC (system A). Thereafter, the crude product is purified by semi-preparative RP-HPLC (system C). The product-containing fractions are lyophilised to give the desired sulfonic acid derivative 3 as a white amorphous powder (13.4 mg, yield 63%).

Example 2.2: Synthesis of Different Radioactive [$^{18}$F]-Mono-Fluoro-Sulfonated Tert-Butyl Esters (3)

Radiosynthesis and subsequent purification are performed using a General Electric TRACERlab MX device. The mono-sultone precursor 2 was engaged with [$^{18}$F]-fluoride at 90° C. for 10 min. Different compositions of the eluent solution used to transfer [$^{18}$F]-fluoride to the reaction vial were tested. The compositions and the results are summarised in Table 1.

TABLE 1

Selected reaction conditions for the preparation of [$^{18F}$]-3 from the mono-sultone precursor 2.

| entry | solvent[a] | phase transfer agent[b] | % conversion rate (radio-HPLC)[c] |
|---|---|---|---|
| 1 | CH$_3$CN | K$_2$CO$_3$/K222 | 3 |
| 2 | CH$_3$CN | Cs$_2$CO$_3$/K222 | 12 |
| 3 | CH$_3$CN + 3% H$_2$O | K$_2$CO$_3$/K222 | 6.5 |
| 4 | CH$_3$CN + 3% H$_2$O | Cs$_2$CO$_3$/K222 | 32 |
| 5 | CH$_3$CN + 6% H$_2$O | Cs$_2$CO$_3$/K222 | 23 |
| 6 | t-BuOH | Cs$_2$CO$_3$/K222 | 86 |
| 7 | Amyl alcohol | Cs$_2$CO$_3$/K222 | 70 |
| 8 | i-PrOH | Cs$_2$CO$_3$/K222 | 90 |

[a] [$^{18}$F]-labelling was carried out in 1.0 mL of the respective solvent (mixture) for 10 min at 90° C. except for entries 4-6 (1.6 mL).
[b] With 1.8 equiv of Kryptofix[K222].
[c] Ratio between product [$^{18}$F]-3 and free Fluorine-18 in the crude reaction mixture.

With respect to acetonitrile as reaction solvent, the use of Cs$_2$CO$_3$ instead of K$_2$CO$_3$ allowed to obtain better results but the conversion rates were still lower than 15% (entry 2). The presence of traces of water in the reaction solvent results in a slight increase of the conversion rate that however remains low (under 30%). The radiofluorination of cyclic sulfonate ester 2 performed in different solvent mixtures named Isopropyl alcohol; amyl alcohol; tert butyl alcohol, makes it possible to produce the [$^{18}$F]-fluorinated tert-butyl ester [$^{18}$F]-3 in good radiochemical yields and purity with respect to all previously performed reactions (entry 6-8).

Example 3: Mono-Fluoro-Sulfonated Benzoic Acid (4)

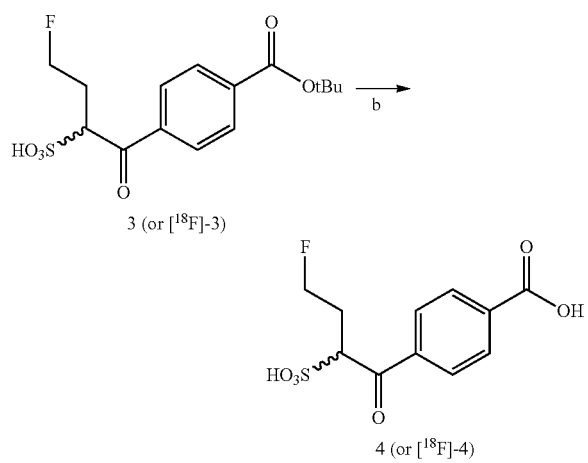

Example 3.1: Synthesis of a Non-Radioactive [$^{19}$F] Mono-Fluoro-Sulfonated Benzoic Acid (4)

To a stirred solution of tert-butyl ester 3 (13.5 mg, 0.04 mmol) in CH2Cl$_2$ (1 mL), is added a solution of TFA in CH$_2$Cl$_2$ (1 mL, 1:1, v/v). The resulting reaction mixture is vigorously stirred at RT for 1 h. Completion of the reaction is checked by analytical RP-HPLC (system A). Then, the reaction mixture is evaporated under reduced pressured and co-evaporated three times with toluene (3×20 mL) to give the desired product 4' as a white solid (11.2 mg, quantitative yield).

Example 3.2: Synthesis of a Radioactive [$^{18}$F] Mono-Fluoro-Sulfonated Benzoic Acid (4)

Following the [$^{18}$F]-radiolabelling and purification steps, the tert-butyl ester of [$^{18}$F]-3 is removed by treatment with 4.0 M aq. HCl instead of TFA (used for the synthesis of the corresponding [$^{19}$F]-derivative). The reaction is performed at 80° C. for 5 min and the resulting free benzoic acid [$^{18}$F]-4 was purified by solid-phase extraction (SPE) using an Oasis® HLB cartridge.

Example 4: [F]-Prosthetic Group (1)

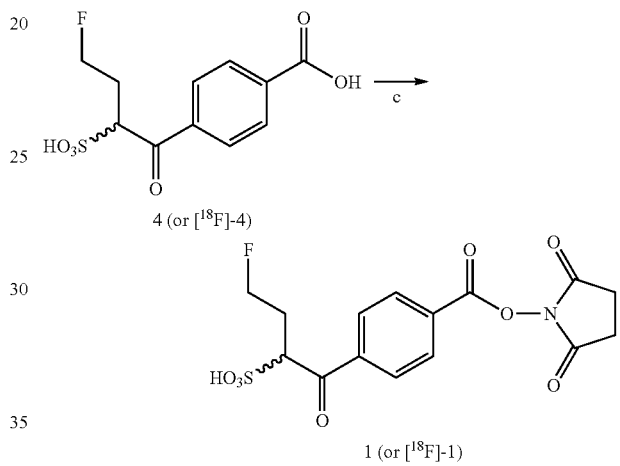

Example 4.1: Synthesis of a Non-Radioactive [$^{19}$F]-Prosthetic Group (1)

Benzoic acid 4 (48 mg, 0.165 mmol) is dissolved in peptide synthesis-grade NMP (1.5 mL). TSTU (49.8 mg, 0.165 mmol, 1 equiv.) and DIEA (165 µL of a 2.0 M solution in NMP, 0.33 mmol, 2 equiv.) are sequentially added and the resulting reaction mixture is stirred at room temperature for 30 min. The reaction is checked for completion by ESI mass spectrometry. The crude NHS ester is used in the next amidification reactions without prior purification-isolation.

Example 4.2: Synthesis of a Radioactive [$^{18}$F]-Prosthetic Group (1)

Final elution of the acidic intermediate from the HLB cartridge with CH$_3$CN-DIEA (9:1, v/v) allows the recovery of the corresponding carboxylate anion which subsequently reacts with a solution of TSTU in CH$_3$CN at 50° C. for 5 min, to provide the corresponding NHS ester. Thus, 3-4 GBq of the targeted [$^{18}$F]-labelled prosthetic compound [$^{18}$F]-1 are obtained within 72 min, starting from 10-15 GBq of [$^{18}$F]-fluoride (35-45% average decay-corrected radiochemical yield for n=15 and 80-95% radiochemical purity).

Example 4.3: Automated Synthesis of Radioactive [$^{18}$F]-Prosthetic Group (1)

A multistep synthesis of this novel prosthetic compound is performed on an automated synthesizer General Electric TRACERlab MX equipped with standard FDG cassettes. A new Excel® sequence, defining every step of the synthetic procedure, is also developed to control the module via a computer. The FDG cassette is composed of three manifolds where solvents and reagents are charged: first manifold (position 1 to 5), second manifold (position 6 to 10) and third manifold (position 11 to 15). The C18 and alumina cartridges are removed and the water bag (250 mL) is transferred from position 7 to 13. A vial of $CH_3CN$ (7 mL) and one containing a solution of TSTU in $CH_3CN$ are respectively placed in positions 3 and 5. All the reactions take place in a single reactor which is cleaned with HCl and deionised water between purification and generation of the active ester. Appropriate detectors permit to follow the radioactivity during the synthesis, on the QMA and HLB cartridges, the reactor and the waste bottle. A Dose Calibrator is used to measure radioactivity into the final recovery vial. Following delivery of [$^{18}$F]-fluoride to the synthesizer module, the radioactivity is isolated on a QMA cartridge, allowing recovery of [$^{18}$O]-H2O. The [18F]-fluoride is eluted with a mixed solution of Kryptofix[K222] (20.8 mg) in $CH_3CN$ (400 μL) and of $Cs_2CO_3$ (9.8 mg) in deionised water (200 μL), and transferred to the reaction vial. After azeotropic evaporation of water with $CH_3CN$ (3×1 mL, 95° C., with a stream of N2 gas), sultone-benzoic acid, tert-butyl ester 2 (3.5 mg) in iPrOH (1 mL) is added. The radiolabelling step is conducted into the reaction vial, at 90° C. during 10 min.

After cooling, the reaction mixture is diluted with water and loaded onto an Oasis® HLB cartridge. The reaction vial and cartridge are washed with water, then the [$^{18}$F]-sulfonated tert-butyl ester [18F]-3 is eluted with an aq. solution of $CH_3CN$ ($H_2O$—$CH_3CN$, 75:25, v/v, 3 mL) and transferred back to the reactor. The tert-butyl ester is then removed by treatment with 4.0 M aq. HCl (2 mL) at 80° C. for 5 min while the HLB cartridge is cleaned with $CH_3CN$ (3 mL) and finally rinsed with water (30 mL). After cooling, the reaction mixture is diluted with water and the [$^{18}$F]-sulfonated benzoic acid [$^{18}$F]-4 is trapped onto the Oasis® HLB cartridge. The reaction vial and cartridge are washed with water, then [$^{18}$F]-sulfonated benzoic acid [$^{18}$F]-4 is eluted with a 10% solution of DIFA in $CH_3CN$ (2 mL) to the reactor. To the formed carboxylate anion, is then added a solution of TSTU in $CH_3CN$ from an external line and activation is performed at 50° C. for 5 min. The reaction mixture is then transferred to the final vial. The reactor is rinsed with $CH_3CN$ (2 mL) and the solution transferred to the final vial. The activity is measured with the Dose Calibrator. [$^{18}$F]-radiolabelling reagent [$^{18}$F]-1 is obtained within 75 min with a moderate 20-30% decay-corrected radiochemical yield (average value from n=10 preparations) and with a 95% radiochemical purity. HPLC (system I): tR=12.1 min.

Example 5: Fluoro-Monosulfonated Cyanine Reference (7)

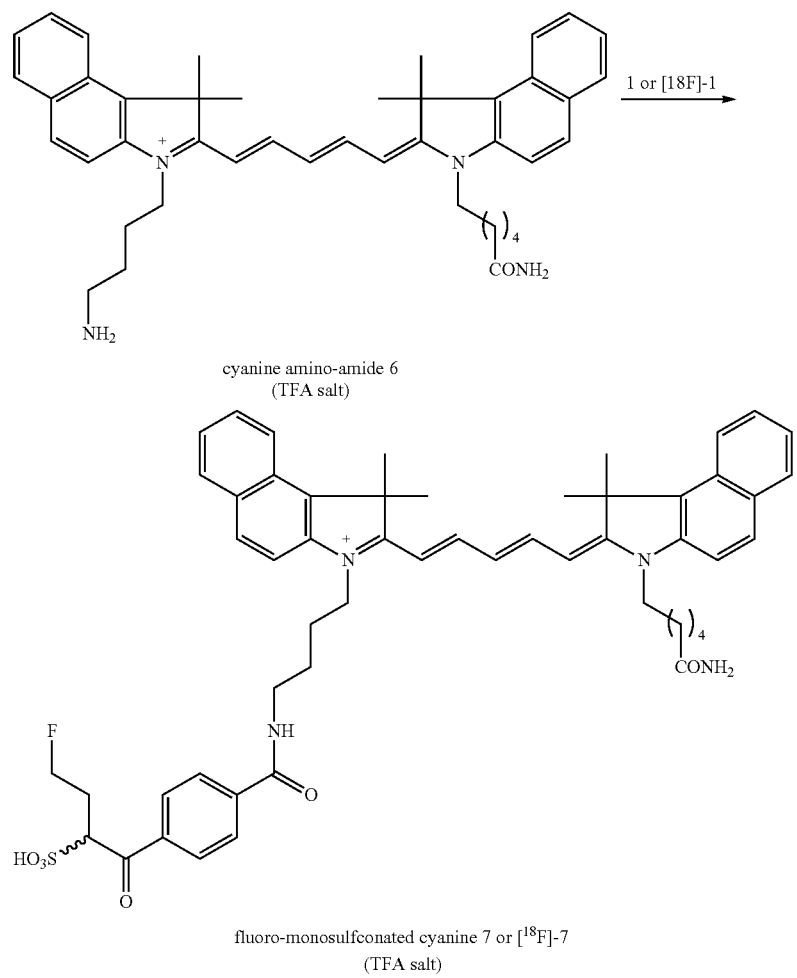

cyanine amino-amide 6
(TFA salt)

fluoro-monosulfconated cyanine 7 or [$^{18}$F]-7
(TFA salt)

Example 5.1: Synthesis of a Non-Radioactive [$^{19}$F]-Fluoro-Monosulfonated Cyanine Reference (7)

Cyanine amino-amide 6 (19.25 mg, 30.1 μmol) is dissolved in NMP (1 mL) and DIEA (180 μL of a 2.0 M solution in NMP, 360 μmol, 12 equiv.). 500 μL of a 90 mM solution of NHS ester 1 in NMP is added and the resulting reaction mixture is stirred at room temperature overnight. The reaction is checked for completion by RP-HPLC (system B). Thereafter, the reaction mixture is diluted with aq. Tetraethylammonium bromide TEAB and purified by semi-preparative RP-HPLC (system E, 1 injection, Rt=42.0-46.0 min). The product-containing fractions are lyophilised and desalted by semi-preparative RP-HPLC (system F) to give the TFA salt of fluoro-monosulfonated cyanine 7 (12 mg, 13 μmol, yield 43%) then lyophilised.

HPLC (system B): Rt=26.0 min, purity>99%;
HPLC (system H): Rt=23.7 min.

Example 5.2: Synthesis of a Radioactive [$^{18}$]-Monosulfonated Cyanine ([$^{18}$F]-7)

Cyanine amino-amide 6 is dissolved in CH$_3$CN containing 1% DIEA. Then, 1.0 mL of the CH$_3$CN solution of [$^{18}$F]-fluorosulfonated NHS ester [$^{18}$F]-1 (vide supra) is added. The vial is vigorously stirred at Room temperature for approximately one min. Thereafter, the reaction is stopped and directly analysed by RP-HPLC (system I with radioactivity detection). HPLC (system I): tR=23.6 min. The retention time difference between the UV and radio traces (ca. 1 min) is caused by the serial arrangement of the detectors. This PET/fluorescent tracer is purified by SPE using an Oasis® HLB cartridge.

Example 6: Fluoro-Monosulfonated Dodecapeptide Reference (8)

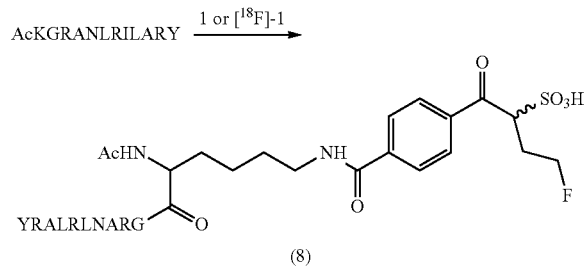

(8)

Example 6.1: Synthesis of a Non-Radioactive [$^{19}$F]-Fluoro-Monosulfonated Dodecapeptide ([$^{19}$F]-8)

A dodecapeptide of sequence AcKGRANLRILARY is dissolved in H2O—CH3CN (1:1, v/v, 500 μL) and 2.6 μL of a 2.0 M solution of DIEA in NMP (5.2 μmol, 4 equiv.) is added. 15 μL of a 90 mM solution of NHS ester 1 in NMP is added and the resulting reaction mixture is stirred at rt overnight. The reaction is checked for completion by RP-HPLC (system G). Thereafter, the reaction mixture is diluted with aq. TFA 0.1% and purified by semi-preparative RP-HPLC (system H, 1 injection). The product-containing fractions are lyophilised to give the TFA salt of fluoro-monosulfonated dodecapeptide ([$^{19}$F]-8).

HPLC (system A): Rt=21.3 mM, purity 96% (two diastereomers); HPLC (system I): Rt=15.2 min; λmax (recorded during the HPLC analysis)/nm 261.

Example 6.2: Synthesis of a Radioactive [$^{18}$F]-Monosulfonated Dodecapeptide ([$^{18}$F]-8)

Dodecapeptide of sequence AcKGRANLRILARY is dissolved in water containing 1% DIEA. Then, 1.0 mL of the CH$_3$CN solution [$^{18}$F]-fluorosulfonated NHS ester [$^{18}$F]-1 (vide supra) is added. The vial is vigorously stirred at room temperature for less than one minute. Thereafter, the reaction is stopped and directly analysed by RP-HPLC (system I with radioactivity detection). HPLC (system I): tR=15.1 min. The peptide-based PET ([$^{18}$F]-8) tracer is purified by SPE using an Oasis® HLB cartridge.

The invention claimed is:
1. A compound of formula (I) or a pharmaceutically acceptable salt thereof:

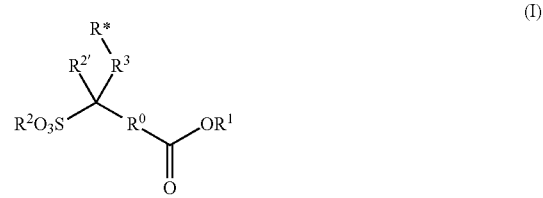

(I)

in which
the R$^0$ bi-functional group is a spacer selected from the group consisting of the following radicals:

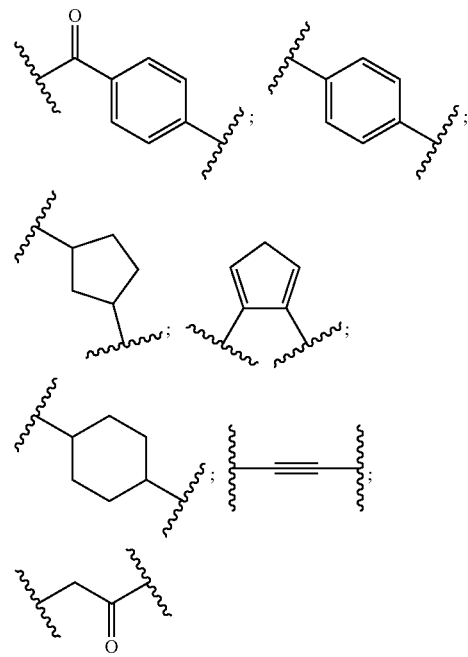

the R$^1$ monovalent group is selected from the group consisting of a succinimidyl ester, a benzotriazole ester, a paranitrophenyl ester, a protecting labile group and hydrogen;
the R$^2$ monovalent group is a hydrogen, a metallic cation, an alkyl, a cyclo-alkyl, an aryl, an arylalkyl, an alkylaryl, an acyl, an alkenyl, an alkynyl radical or a combination of these radicals;

the $R^{2'}$ monovalent group is hydrogen or an alkyl, a cyclo-alkyl, an aryl, an arylalkyl, an alkylaryl, an acyl, an alkenyl, an alkynyl radical or a combination of these radicals;

the $R^3$ bi-functional group is moiety $(CR^4R^5)_n$—, wherein $R^4$, $R^5$ are each individually selected from the group consisting of hydrogen, an alkyl, a cycloalkyl, an aryl, an arylalkyl, an alkylaryl, an acyl, an alkenyl, an alkynyl and a mixture thereof, wherein n is an integer between 1 and 3; and $R^*$ is a (radio) nuclide.

2. The compound according to claim 1, wherein said compound to is represented by formula (II):

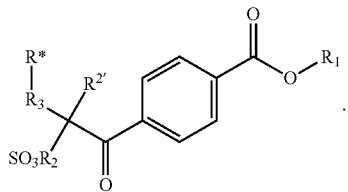

(II)

3. The compound according to claim 1, wherein said compound to is represented by formula (III):

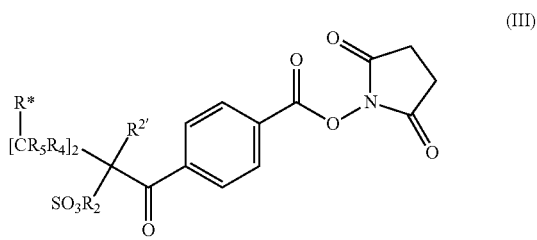

(III)

wherein $R^4$ and $R^5$ are hydrogen.

4. Drug or diagnosis product comprising at least one compound according to claim 1, and a pharmaceutically acceptable carrier.

* * * * *